United States Patent [19]

Smith

[11] 3,975,157
[45] Aug. 17, 1976

[54] GEOCHEMICAL EXPLORATION USING ISOPRENOIDS

[75] Inventor: Melvin E. Smith, Bartlesville, Okla.

[73] Assignee: Phillips Petroleum Company, Bartlesville, Okla.

[22] Filed: July 21, 1975

[21] Appl. No.: 597,605

[52] U.S. Cl. .................................. 23/230 EP
[51] Int. Cl.² ..................................... G01N 31/08
[58] Field of Search ......................... 23/230 EP

[56] References Cited
UNITED STATES PATENTS 2,854,396  9/1958  Hunt et al. .............. 23/230 EP X
3,847,549  11/1974  Schorno .................... 23/230 EP

OTHER PUBLICATIONS

Bayliss, "Formation of Pristane, Phytane, & Related Isoprenoid Hydrocarbons . . ." Chem. Abstr., vol. 71, 1969, No. 114914x.

Brooks et al., "Isoprenoid Hydrocarbons in Coal & Petroleum," Nature, vol. 222, Apr. 19, 1969, pp. 257–259.

Primary Examiner—Morris O. Wolk
Assistant Examiner—Arnold Turk

[57] ABSTRACT

A geochemical exploration technique wherein petroleum source rocks are characterized on the basis of an Isoprenoid Generation Index, IGI, which is the ratio of the relative concentrations of the 20-carbon isoprenoid and the sum of the 18 and 16 carbon isoprenoids. Organic extracts of rocks in which diagenesis has not proceeded far enough to have produced migratable petroleum have an IGI of 3 or greater, whereas crude oils and extracts of source rocks have lower values. The IGI is used to calculate other, origin-diagnostic parameters useful in correlating oils and extracts of marine origin.

4 Claims, 3 Drawing Figures

GEOCHEMICAL EXPLORATION USING ISOPRENOIDS

This invention relates to geochemical exploration.

Hydrocarbon energy sources such as petroleum and natural gas are found in commercial quantities in subsurface rock formations such as sandstones and limestones. Since the presence of such hydrocarbonaceous materials in a subterranean formation is not ordinarily manifested by readily discernible surface indicia, various techniques have been developed to aid in exploring for oil and gas. One such technique is geochemical exploration.

Petroleum geochemistry utilizes the fundamental concepts of genesis, migration and accumulation of petroleum in the development of procedures for use in exploration and development programs.

In most geochemical exploration methods, a search is made, generally at or near the surface of the earth, to determine the presence of components of petroleum, precursors of petroleum, or derivatives thereof. These procedures are based upon the theory that these hydrocarbonaceous materials are fugitive and have migrated to or near the surface of the earth from an underlying petroleum reservoir. The presence of such hydrocarbonaceous materials which are normally constituent components of petroleum has been found to be indicative of the presence of a subterranean reservoir of petroleum in the general area.

However, such surface methods of geochemical exploration give little indication of the location of the underlying petroleum reservoir. Other exploration procedures such as seismic surveying can be utilized to identify the possible petroleum reservoirs at subterranean locations in the earth's crust. Such methods give valuable information as to subterranean structures favorable to the accumulation of petroleum; however, these methods are ineffective in determining which, if any, of such structures actually contain petroleum deposits.

In order to adequately evaluate whether such subsurface structures contain petroleum, in recent years there has been developed geochemical exploration techniques based upon the so-called "source rock" concept. Under this concept, it is assumed that petroleum hydrocarbons are formed during long periods of burial in fine-grained sediments of high organic matter content, the petroleum hydrocarbons being derived from organic matter of biologic origin which was deposited with these sediments in an aqueous, usually marine environment. The exact mechanism by which oil and/or gas are formed in such sediments, i.e., source rocks, is not known with certainty. Generally, it is presently considered that the transformation of the original organic matter contained in such sediments is effected in a first stage before deep burial of the sediments by biogenic processes which must necessarily include an oxidant such as molecular oxygen, elemental sulfur, sulfate ions, and the oxidized states of certain heavy metals, e.g., ferric hydroxide. As the sediments become more deeply buried, the transformation of the remaining unconverted organic matter is thought to be effected abiogenetically. These processes, i.e., biogenic and abiogenic, are considered to be responsible for what can be termed the primary and secondary genesis of petroleum, respectively. After the hydrocarbon forming mechanism has taken place, it is thought that the petroleum hydrocarbons in the source rock then migrated to more permeable reservoir rocks where they accumulated in the concentrated deposits found today.

The application of the concepts of petroleum geochemistry to subsurface exploration problems thus involves the evaluation of shale and limestone sidewall cores and core samples to determine whether the rock is or can be a source rock. The objective of such evaluation is the ascertainment of likely sources for petroleum and estimation of their productivity. Such source rock evaluations permit outlining areas favorable to prospecting because of the proximity to rocks geochemically identified as having generated petroleum and from which oil has subsequently migrated.

By definition, a source rock is a rock in which significant quantities of oil have been generated and from which the petroleum has migrated. Nonsource rocks are subdivided into barren rocks which are devoid of organic matter, lean rocks which contain a low concentration of organic matter, and immature rocks which may contain an adequate amount of organic matter of the proper quality to be source rocks but have not undergone major genesis of petroleum because of insufficient time or depth of burial. The rate of petroleum genesis is considered to be a function of the depth of burial because of the positive geothermal, i.e, temperature, gradient, and not of the higher pressure encountered at deeper depths. Source rocks, therefore, should be evident in a basin early in the exploration. Their absence should be taken as a basis for concern. It follows that it is important to ascertain the maturity of the rock in order to determine whether deeper drilling in the area, assuming the presence of suitable structure, would be justified.

In previous geochemical exploration techniques utilizing the source rock concept, rock formations have been characterized as source rocks on the basis of the amount and kind of hydrocarbons contained in the formation. Exemplary of such techniques are the procedures disclosed in the article by Bray et al., "Distribution of N-Paraffins as a Clue to Recognition of Source Beds." Geochemica et Cosmochemica acta. 1961, Vol. 22, pages 2–15 and in U.S. Pat. Nos. 2,854,396 and 3,446,597. While such techniques are promising tools in exploration for oil, they are not without limitations.

Current applications of geochemistry to the solution of subsurface exploration problems utilizing the source rock concept have resulted in a number of procedures which have been of value in the exploration for and development of commercial oil and gas fields. The procedures presently available have been effective for determining whether or not a sedimentary formation, which may be relatively barren of hydrocarbon content, is a likely source rock for petroleum hydrocarbons, including gaseous petroleum hydrocarbons, and also for determining the state of maturation for such sediments. However, these methods fail to provide any indicia for ascertaining the likelihood that deeper formations could be source rocks for petroleum hydrocarbons.

It is an object of this invention to provide a method for the geochemical exploration for petroleum hydrocarbons.

It is another object of this invention to provide a method for determining the state of maturation of a subterranean geological formation.

It is yet another object of this invention to provide a method for determining whether there exists in a particular area favorable conditions for the generation and accumulation of petroleum hydrocarbons.

These and other objects and advantages of the present invention will be readily apparent from a reading of the present disclosure, appended claims and the drawings of which:

Figure 1:
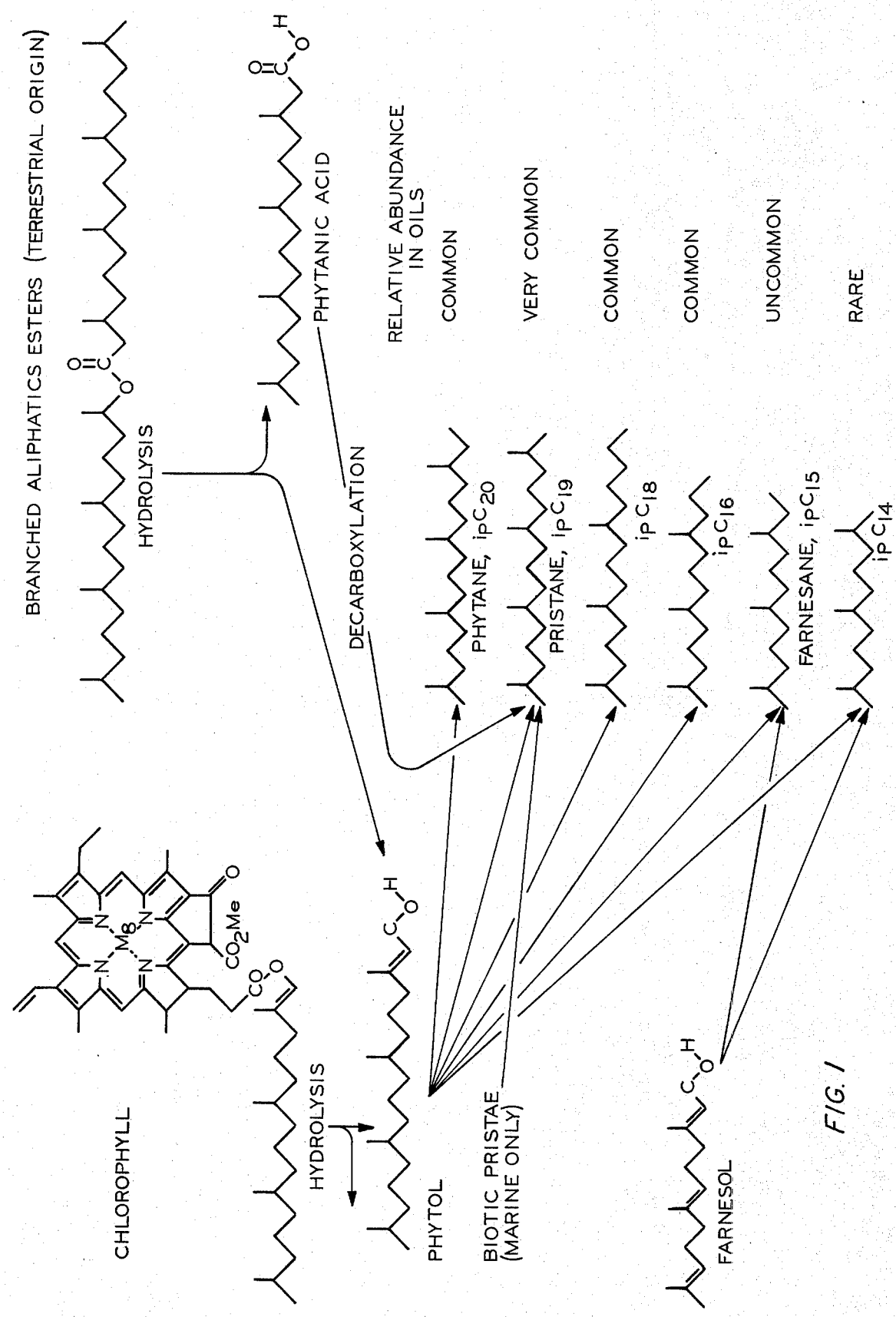
FIG. 1 illustrates the origins of isoprenoid hydrocarbons.

In accordance with the present invention, there is provided a new and improved geochemical exploration method involving the identification of petroleum source rock sediments on the basis of isoprenoid hydrocarbons.

The present invention provides a method for determining whether or not a sedimentary formation which may be relatively barren of hydrocarbon content, is a likely source rock for petroleum hydrocarbons, and also for determining the state of maturation for such a sediment.

The present invention also provides a method for correlating a petroleum with a source rock.

This invention further provides methods for correlating two or more crude oils to determine whether or not such oils are of common origin.

To more fully appreciate the invention, the definition and meaning of certain words of art as they are used throughout the specification and appended claims are as follows:

Normal paraffins are linear alkane chains terminating in methyl ($CH_3$) groups.

Source rocks are rocks in which significant quantities of petroleum have been generated and from which the petroleum has migrated.

Nonsource rocks include barren, lean, and immature rocks.

Barren rocks are those devoid of organic matter.

Lean rocks are those containing low concentrations of organic matter.

Immature rocks are those which may contain an adequate amount of organic matter of the proper quality to be source rocks but have not undergone major generation of petroleum because of insufficient time or depth of burial, i.e., insufficient heat.

Diagenesis denotes the changes in organic material as functions of time, temperature, pressure and catalysis. The result of diagenesis is the genesis, i.e., generation of petroleum.

OEP or odd-even predominance is the ratio of odd carbon number paraffin concentrations to even number paraffin concentrations of $C_{10}$–$C_{35}$ normal alkane hydrocarbons.

OEP or average odd-even predominance is the ratio of odd-carbon-numbered to even-carbon-numbered $C_{25}$–$C_{33}$ normal alkanes in any given sample.

Isoprenoids are 2,6,10,(14)-tri(tetra) methylalkanes which contain from 14 to 20 carbon atoms per molecule. They form a group of structurally related compounds. Other isomers such as 2,6,11,15-tetramethylhexadecane and compounds of similar carbon structure of a greater or lesser number of carbon atoms are also commonly termed isoprenoids.

The environments of deposition are defined by the following characteristics:

Terrestrial, wherein the organic material stems from land plants which are characteristically waxy to minimize loss of moisture. The fauna contribution is relatively low.

Lacustrine, wherein the organic material stems from aqueous plants which do not require waxy coatings. The fauna contribution is relatively low. Only large lakes or lakes with arid shorelines and a few tributary rivers constitute a significant lacustrine environment. Small lakes and swamps receive a significant terrestrial organic contribution and lacustrine organic matter is of minor importance.

Marine, which is sufficiently removed from terrestrial sources for all organic material to have been extensively re-worked biologically prior to incorporation into the sediment. The fauna and lipid content is relatively high.

Brackish, which is a mixture of terrestrial and marine, such as found in deltas, tidal swamps and the like.

The isoprenoids are hereinafter referred to by the notation ipC20, ipC19, etc., to designate the isoprenoid with 20 carbon atoms, 19 carbon atoms, etc. The suffixes "A" and "F" are used to designate isoprenoids abiotically generated from Phytol and Farnesol, respectively; "B" is used to designate isoprenoids of direct biological origin; and "T" is used to designate the total of that carbon number.

Compounds containing the isoprenoid carbon skeleton are common biological constituents. Once divested of functional groups and reduced to alkanes the structure is highly resistant to physical or biological alternation after sedimentation in an anaerobic environment. Isoprenoids are aerobically biodegradable, but only slowly and only after depletion of n-alkanes and branched chain alkanes containing only one methyl branch, attached to the second or third carbon of the carbon chain.

All isoprenoids up to a carbon number of 25 have been reported to occur in crude oils: however, only those six shown in FIG. 1 commonly occur in sufficient abundance to be of routine geochemical interest.

Of several naturally-occurring compounds, Phytol is generally accepted as the precursor of the bulk of the common isoprenoids in petroleum. Phytol occurs as an ester-linked side chain of chlorophyll, which is a major source of organic material in recent sediments. Marine planktonic algae have been estimated to be the source of 90 percent of the world production of chlorophyll; hence, they provide abundant source material in the marine environment which is the source of most petroleums. Phytol is hydrolyzed from the chlorophyll molecule by small crustaceans which are important intermediates in the food chain between algae and higher organisms.

Farnesol, which replaces Phytol in certain bacterial chlorophyll is also accepted as a possible precursor of isoprenoids with 15 or less carbon atoms, although because of lower abundance, the contribution is often small.

Of all the isoprenoids, only pristane, ipC19, is thought to be biologically produced and incorporated into the sediment as the stable alkane. Analyses of zooplankton have shown that the copepod genus Calanus, living predominately in cold waters on a phytoplankton diet, contains up to 100 times as much pristane as other biota and about 10 times more pristane as other genera living in warmer water. It has been found that in starving Calanus, pristane is utilized less for energy than are other lipid components; thus, dying Calanus can be expected to incorporate pristane into the sediment. The key position of Calanus in the marine food chain suggests that Calanus may be a primary source of pristane in the marine environment.

Another source of isoprenoids is thought to be the non-crystalline highly-branched aliphatic ester fraction of the waxy protective coatings and cuticles of land plants. It has been shown that these waxy coatings and cuticles undergo diagenesis in the presence of water and insoluble organic matter such as coal, kerogen, or clay in lieu of organic, to yield pristane, ipC19, and phytane, ipC20, as principle products.

Thus, the multiple precursors of the isoprenoids each represent a unique factor of the sediment and reflect the organisms and detritus which existed as a result of the prevailing ecological and environmental conditions existing at the time of sedimentation.

As shown in FIG. 1, phytane (ipC20), pristane (ipC19), ipC18, ipC16, ipC15 and ipC14 are products of the diagenesis of phytol, which is derived by the hydrolysis of chlorophyll or the plant esters. Pristane, ipC19, is also the product of hydrolysis and decarboxylation of the plant esters. Biotic pristane is chemically and physically identical to and cannot be distinguished from pristane derived from phytol. The amount of biotic pristane is fixed by the composition of the sediment and remains unchanged, whereas the amount of pristane and other isoprenoids stemming from phytol depend not only on the amount of phytol in the sediment but also on the extent of phytol diagenesis. The diagenesis of farnesol also provides isoprenoids of 15 or less carbon atoms.

Phytane, ipC20 is the major product of early diagenesis. With more advanced diagenesis, relatively greater amounts of the lower molecular weight isoprenoids are generated.

Thus, in accordance with one embodiment of this invention there is provided a method of geochemical exploration which comprises the steps of
a. obtaining at least one rock sample from at least one location in the earth's crust, and
b. analyzing the sample for isoprenoids to determine the ratio between the relative concentration of ipC20 and the lower isoprenoids.

In one aspect, the ratio ipC20/ipC19A is used, wherein ipC19A is abiotically generated pristane from phytol.

In another aspect, the ratio ipC20/(ipC18 + ipC16) is used. This ratio is termed the Isoprenoid Generation Index (IGI). The sum of ipC18 and ipC16 is considered more accurate than either of these low-concentration components alone. Organic extracts of rocks in which diagenesis has not proceeded far enough to have produced migratable petroleum have an IGI of 3 or greater, whereas crude oils and extracts of source rocks have lower values. A given value of IGI denotes the same degree of diagenesis for all crude oils and rock extracts regardless of the environment of deposition or the source and composition of the organic constituents in the sediment. The IGI of crude oils is a measure of the degree of diagenesis at the time the crude oil migrated from the source rock and remains unaltered by subsequent maturation reactions.

An advantage of this invention is that IGI can be measured for samples in which biodegradation has destroyed the n-alkanes, consequently preventing determination of $\overline{OEP}$. Another advantage is that IGI appears to correlate for oils or extracts of diverse origin. For crude oils and/or rock extracts of common origin $\overline{OEP}$ reflects the relative degree of diagenesis. For oils and/or extracts of diverse origin, insofar as there is variation in the relative amounts of the multiple precursors of n-alkanes, $\overline{OEP}$ does not correlate with the degree or extent of organic diagenesis. In contrast, the IGI does appear to correlate.

As an absolute measure of the degree of generation of crude oils and rock extracts from organic material, IGI is considered superior to $\overline{OEP}$. IGI measures the degree of diagenesis of a single precursor, phytol, and ranges from high values to near zero as the extent of organic diagenesis advances. $\overline{OEP}$ on the other hand, results from the dilution of n-alkanes of predominately odd (or sometimes even) carbon numbers of early diagenetic origin by a flood of n-alkanes of less odd or even predominance generated from other precursors during later diagenesis. $\overline{OEP}$ ranges from considerably greater than or occassionally less than unity to near unity as diagenesis proceeds.

Figure 2:
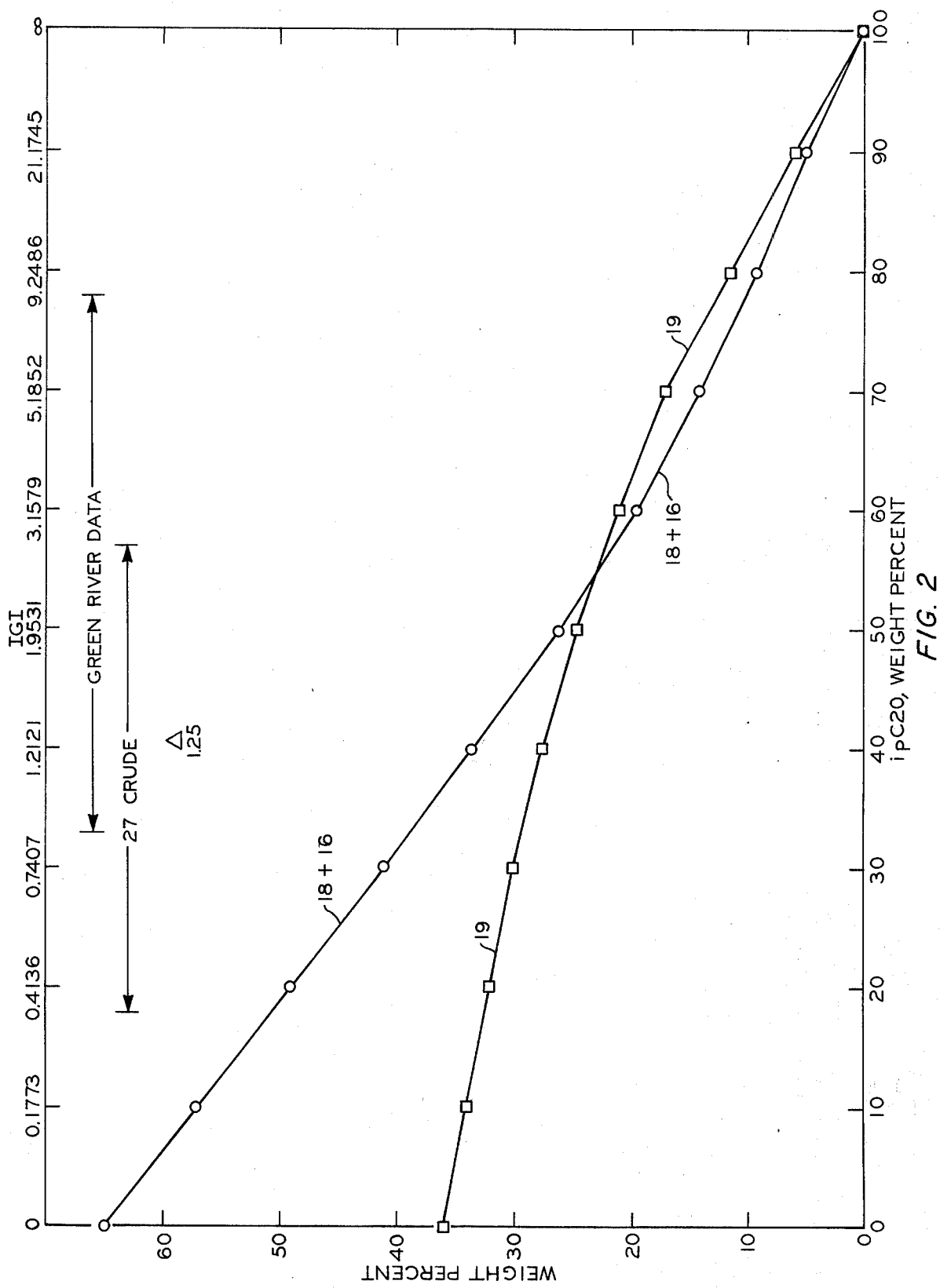
FIG. 2 illustrates the relationship between the predominate isoprenoid hydrocarbons in Green River Shale.

The IGI can be used to derive other parameters which are useful tools for geochemical exploration. FIG. 2 is a plot of the amounts of ipC16, ipC18 and ipC19 relative to the amount of ipC20 in shale from the Green River Basin in Wyoming. The isoprenoids in the Green River Shale are believed to stem from a single source, i.e., phytol from chlorophyll. There are four lines of evidence to support this assumption. First, paleontological evidence indicates that the environment of deposition was warm lacustrine, as opposed to cool marine waters; thus, biotic pristane should be absent. Seconds, the borehole from which the cores were taken was along the axis of the basin and situated relatively distant from influxes of terrestrial detritus. The organic material in the Green River formation has been attributed to an algal ooze of fecal pellets. There is little paleobotanical evidence that higher plants contributed significantly to the branched aliphatic hydrocarbons of the Green River oil shale, and the n-alkane distribution of extracts from this core favors the lower molecular weight range typical of algal lipids, i.e., n-C17 and not n-C29. Algal lipids and bacteria do not contain significant quantities of isoprenoids and algae do not contain the waxy esters of terrestrial plants. Therefore, isoprenoids originating from land flora are not of significant contribution to this particular Green River core. Third, there is stereochemical evidence that phytol is the only precursor to the isoprenoids found in the Green River Shale. Fourth, on the basis of regression analysis it is thought that Green River isoprenoids having 20, 19 and 18 carbon atoms stem from a common precursor.

FIG. 2 represents the accrued products of diagenesis of phytol. The data from a number of isoprenoid analyses were normalized to ipC20 + ipC19 + ipC18 + ipC16 = 100 and then plotted. The IGI scale at the top of the plot is at infinity (zero genesis) at ipC20 = 100, and ipC19, ipC18 and ipC16 = 0. At this point an infinitely small amount of phytol has undergone diagenesis to produce phytane, ipC20. As diagenesis progresses, the relative concentrations of accrued products shifts to the left. The ranges of genesis of the Green River Shale extracts and of 27 crude oils are shown. The mean value of IGI for the crude oils is 1.25.

Using the IGI, the amount of pristane from phytol, i.e., abiotic pristane, ipC19A, is calculated as follows:

At the IGI of the sample a vertical line is extended downwardly to intercept the curves of ipC19 and (ipC18 + ipC16). A line is drawn tangent to each curve at the point of intercept. The slope and intercept of each tangent is then determined and applied to the following equations:

$$(\overline{18} + \overline{16}) = m\overline{20} + b \tag{1}$$

where $m$ and $b$ are the slope and intercept, respectively, of the line drawn tangent to the $(\overline{18} + \overline{16})$ curve at the point of intercept of the IGI of the sample;

$$\overline{19A} = m'\overline{20} + b' \tag{2}$$

where $m'$ and $b'$ are the slope and intercept, respectively, of the tangent to the ipC19 curve.

In equations (1) and (2), the bar over the figure denotes that the value is normalized to $\overline{20} + \overline{19A} + \overline{18} + \overline{16} = 100$.

Equation (1) is solved for $\overline{20}$ $$\overline{20} = \frac{(\overline{18} + \overline{16}) - b}{m} \tag{3}$$

Equation (2) is divided by equation (3) to obtain an expression for $\overline{19A}$.

$$\frac{\overline{19A}}{\overline{20}} = \frac{m(m'\overline{20} + b')}{(\overline{18} + \overline{16}) - b}$$

$$\overline{19A} = \frac{m(m'\overline{20} + b')}{(\overline{18} + \overline{16}) - b} \overline{20} \tag{4}$$

Equation (4) requires that all values be normalized. However, gas-liquid chromatographic (GLC) analyses cannot be normalized because $\overline{19A}$ is unknown, i.e., the GLC will measure the total, 19T, but cannot distinguish biotic pristane from pristane derived from phytol. The measured quantities of each isoprenoid expressed below enclosed in parentheses have the following relationships:

$$\overline{20} = \frac{(20)}{(20) + (18) + (16) + (19A)} \tag{5}$$

$$\overline{18} = \frac{(18)}{(20) + (18) + (16) + (19A)} \tag{6}$$

$$\overline{16} = \frac{(16)}{(20) + (18) + (16) + (19A)} \tag{7}$$

$$\overline{19A} = \frac{(19A)}{(20) + (18) + (16) + (19A)} \tag{8}$$

where (19A) is the amount of pristane from phytol which the GLC would measure if it could distinguish such pristane from biotic pristane.

Equations (5), (6), (7) and (8) are substituted into equation (4) and solved to provide a quadratic equation of the form $ax^2 + bx + c = 0$, where $x = (19A)$ as follows $$b(19A)^2 + [(20)(b + mb') + ((18) + (16))(b-100)](19A) + [(20)^2(mb' + mm'100) + mb'(20)((18) + (16))] = 0 \tag{9}$$

Equation (9) thus permits the determination of pristane from phytol. By subtracting this quantity from the total pristane, the pristane of biotic origin is determined:

$$ipC19B = ipC19T - ipC19A \tag{10}$$

Because of the possible differences in degree of diagenesis between samples, it is necessary to make the comparison of the pristane content at a fixed state of genesis which either has been or could ultimately be achieved. The quantity of biotic pristane remains unchanged by genesis; as illustrated by FIG. 2, the total pristane increases with increasing genesis. A parameter designated as the Pristane Index (P.I.) has been defined as the ratio of Biotic Pristane to Total Pristane which will be or was present at a fixed degree of genesis as measured by IGI, preferably when the IGI is 1.25:

$$P.I. = \frac{(19B)}{(19A)_{1.25} + (19B)} \tag{11}$$

The Pristane Index can be used to map rock units according to the characteristic paleoecology of their organic source material regardless of the degree of diagenesis and correlated with petroleum generated therefrom. Thus, immature source rock can be correlated with petroleum generated from a more mature portion of the source rock facies deposited elsewhere in the reservoir. Crudes of common origin can also be identified even though they may have stemmed from source rock units having different geothermal gradients or catalytic constituents to have altered the degree of diagenesis.

The Pristane Index is calculated as follows:

At the IGI of the sample a vertical line is extended downwardly to intercept the curves of ipC19 and (ipC18 + ipC16). Lines are drawn from each of these intercept points to the points of intercept at IGI = 1.25. For each of these lines the slope and intercept values are determined and applied to the following equations:

$$(\overline{18} + \overline{16}) = M\overline{20} + B \tag{12}$$

where $M$ and $B$ are the slope and intercept, respectively, of the line drawn from the intercepts of the sample IGI and IGI$_{1.25}$ and the (ipC18 + pC16) curve; and $$\overline{19A} = M'\overline{20} + B' \tag{13}$$

where $M'$ and $B'$ are the slope and intercept, respectively, of the line drawn from the intercepts of the sample IGI and IGI$_{1.25}$ and the ipC19 curve.

In equations (12) and (13), the bar over the figure denotes that the value is normalized to.

$$\overline{20} + \overline{19A} + \overline{18} + \overline{16} = 100 \tag{14}$$

Equation (14) is solved for $\overline{20}$ and substituted into (12):

$$(\overline{18} + \overline{16}) = \frac{M(100 - \overline{19A}) + B}{1 + M} \tag{15}$$

Equation (13) is solved for $\overline{20}$:

$$\overline{20} = \frac{\overline{19A} - B'}{M'} \tag{16}$$

Equation (16) is divided by (15):

$$\frac{\overline{20}}{(\overline{18}+\overline{16})} = IGI = \frac{(\overline{19A} - B')(1+M)}{M'[M(100-\overline{19A})+B]} \qquad (5)$$

Solve for 19A:

$$\overline{19A} = \frac{(100MM' + BM')IGI + B'(1+M)}{MM' IGI + (1+M)} \qquad (17)$$

Equation (17) allows the calculation of $\overline{19A}$ at any value of IGI. This value is used in the following equation to calculate the quantity of ipC19A at an IGI of 1.25:

$$(19A)_{1.25} = (19A)_n \times \frac{\overline{19A}_{1.25}}{\overline{19A}_n}$$

where $n$ is the value of IGI for the sample.

The calculated value for $(19A)_{1.25}$ is used, together with the value for ipC19B, to calculate the Pristane Index, according to equation (11):

$$P.I. = \frac{19B}{(19A)_{1.25} + (19B)} \qquad (11)$$

For marine oils, the Pristane Index is origin-diagnostic and independent of the degree of genesis or maturation in a source rock.

If applied to oils of terrestrial origin, the quantity calculated to be pristane of biotic origin actually stems from sources such as the diagenesis of the pristanic acid moiety of plant waxes and is dependent on the state of diagenesis. The resultant Pristane Index is of limited, but some origin-diagnostic value. A Pristane Index of near zero for such oil or extract indicates that the oil or rock stems from a lacustrine environment. Oils of both common origin and equivalent states of genesis will have the same Pristane Index.

The Pristane Index can be extended to oils or extracts of brackish origin if they have a Pristane/Phytane ratio of 1.0 or less, which indicates that any contributions of terrestrial plant waxes were biodegraded before incorporation into the sediment. The Pristane Index can also be extended to oils or extracts of brackish origin having a Pristane/Phytane ratio of greater than one, when the IGI's of the oils, extracts or oil/extract pairs are approximately equal.

The third precursor of isoprenoids is farnesol, which replaces phytol in certain bacterial chlorophyll. Farnesol is generally accepted as a precursor of isoprenoids having 15 or less carbon atoms. The contribution from farnesol is generally small.

Figure 3:
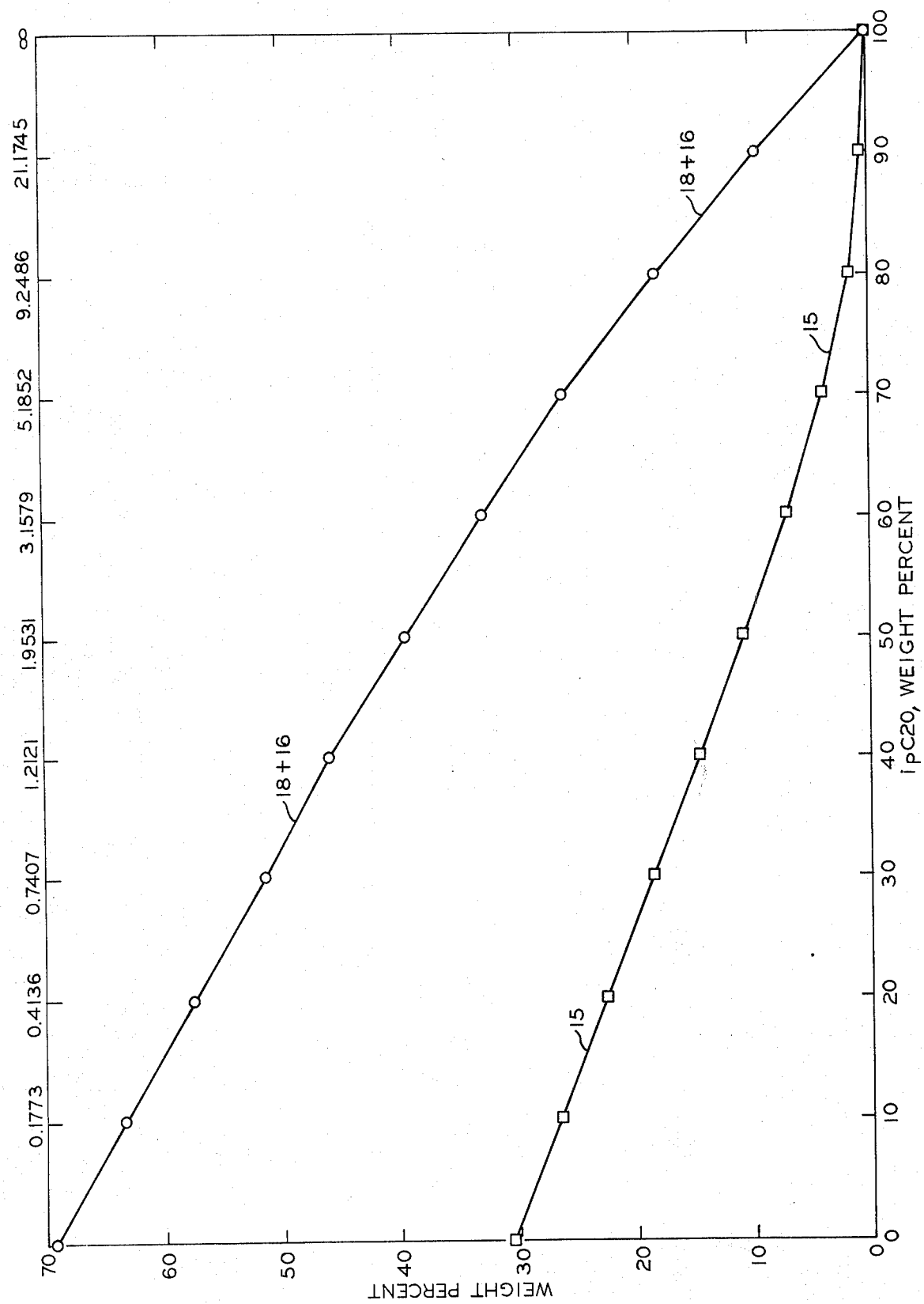
FIG. 3 illustrates the relationship between the C20, C18, C16 and C15 isoprenoid hydrocarbons.

The determination of farnesane, ipC15, generated from phytol is made in a manner similar to the determination of pristane from phytol. The data are normalized to $\overline{20} + \overline{18} + \overline{16} + \overline{15} = 100$, and then plotted as shown in FIG. 3. Substituting 15A and $\overline{15A}$ for 19A and $\overline{19A}$, respectively, in equations 1–9 above, there is derived the following quadratic equation:

$$b(15a)^2 + [(20)(b + mb') + ((18) + (16))(b - 100)](15A) + [(20)^2(mb' + mm'100) + mb'(20)((18) + (16))] 0 \qquad (18)$$

Equation (18) thus permits the determination of farnesane from phytol. By substracting this quantity from the total farnesane, the farnesane from farnesol is determined:

$$ipC15F = ipC15T - ipC15A \qquad (19)$$

Compositional data for ipC14 in the Green River Shale, discussed above, are unavailable; however, it is assumed that ipC14 is proportioned between phytol and farnesol sources the same as farnesane, ipC15.

The relative amounts of isoprenoids from each of the three precursors, i.e., phytol, biotic pristane and farnesol, is a unique origin-diagnostic characteristic of a crude oil or rock extract. For oils and extracts, the weight fractions from phytol, biotic and farnesol origins are defined as the Isoprenoid Profile, which is calculated as follows:

$$\text{Phytol Isoprenoids} = \frac{ipC20 + ipC19A + ipC18 + ipC16 + ipC15A + ipC14A}{\text{Total Isoprenoids}} \qquad (20)$$

$$\text{Biotic Pristane} = \frac{ipC19B}{\text{Total Isoprenoids}} \qquad (21)$$

$$\text{Farnesol Isoprenoids} = \frac{ipC15F + ipC14F}{\text{Total Isoprenoids}} \qquad (22)$$

Oils or extracts having the same or nearly the same Isoprenoid Profile at the same or nearly the same IGI stem from a common source.

The invention can be employed as a primary exploratory technique to determine the possibility of petroleum accumulations within a general geographical area of the earth's surface. In this case, it usually will be necessary to obtain samples from a large number of locations in the earth's crust. The samples can be obtained either at the surface of the earth or by drilling to subsurface locations in the earth's crust.

The instant invention can also be employed as a supplemental exploratory tool in areas in which other prospecting operations have already been carried out. For example, seismic surveying of a particular locality may indicate the presence of subsurface sedimentary structures within which petroleum hydrocarbons may be accumulated. In this case, the instant invention can provide a valuable tool in determining which one of a plurality of subsurface structures favorable to the accumulation of hydrocarbons may actually contain petroleum deposits.

The instant invention can also be employed to correlate extracts of rocks with crude oils or seep oils to determine whether the rock is the geochemical source of the oil.

Analyses of the source rock, crude oil or seep oil for the amounts of isoprenoids can be carried out in any suitable procedure. Care must be taken to employ a procedure which will give accurate results considering the small amounts of isoprenoids generally found in oils or rocks. If the sample to be analyzed is a possible source rock, the rock is cleaned and dried, then crushed by conventional means to produce relatively small granules which can then be ground to a size suitable for extractions of the organic materials.

The organic material is then extracted from the sample with a suitable solvent, e.g., methylene chloride. Exhaustive extraction by such means as Soxhlet extraction apparatus, at or near the boiling point of the solvent is presently preferred. The solvent can be evaporated from the extract by suitable means such as rotary vacuum evaporators and the like.

The extract is then chromatographed on a silica gel column using n-pentane as the elutant to isolate the saturated hydrocarbons, including the isoprenoids. The normal alkanes are removed from the eluate by urea adduction. The non-adduct solution is then chromatographed on a fresh silica gel column using n-pentane as the elutant, to isolate the remaining saturated hydrocarbons. The n-pentane is removed from the eluate by evaporation. The sample is then taken up in an anhydrous benzene/methanol 3/1 mixed solvent and then a saturated solution of thiourea in anhydrous methanol is added to adduct the isoprenoids. After a suitable period the non-adduct solution is removed.

Cyclohexane and hot distilled water are added to the dry thiourea-isoprenoid adduct crystals. The hot water decomposes the thiourea and releases the isoprenoids into the cyclohexane. The cyclohexane-isoprenoid solution is then analyzed by GLC to determine the relative quantities of isoprenoids, and not their concentration in the source rock or oil.

The following examples illustrate the invention:

EXAMPLE I

A group of 29 crude oils was selected for testing. The oils listed in Table I below were selected to cover a wide range of geological time and to include considerable diversity in physical properties and gross chemical constitution. Included are two pairs and two trios of crude oils previously determined to be of common origin.

Each of the samples was chromatographed on silica gel, then adducted with urea to remove the normal alkanes. The non-adduct solutions were chromatographed on a fresh activated silica gel-n-pentane column using 7 ml of silica gel per each ml of the urea non-adduct solution. The urea non-adduct solution was added to the top of the column. 25 ml of n-pentane was added. 6 psig of nitrogen pressure was applied to the column. The column outlet valve was opened to pass the n-pentane through the column into a round-bottom flask.

The n-pentane was removed from the flask by evaporation. The hydrocarbons remaining in the flask were transferred by washing with dichloromethane to a weighed vial. The dichloromethane was removed by evaporation and the vial was reweighed to determine the weight of hydrocarbon in the vial.

To the sample in the vial was added first anhydrous benzene/methanol 3/1 mixed solvent and then a saturated solution of thiourea in anhydrous methanol. A minute amount of methyl ethyl ketone was added to the vial which was then capped, shaken to mix the contents and allowed to stand at room temperature for about 14 hours.

Thereafter, the clear liquid was removed without disturbing the crystals. The crystals were then dried by evaporation.

To the crystals in the vial were added cyclohexane and hot water. The thiourea decomposed and released the isoprenoids into the cyclohexane. The cyclohexane layer was analyzed for isoprenoids by GLC, using a 150 ft. 0.01 inch ID column in a Perkin-Elmer 900 GLC programmed from 50° to 200°C at 10°C per minute.

The results of the Isoprenoid analyses are given in Table I below:

Table I

| Source M.Y.[1] | Producing M.Y.[2] | Formation Period | Name | Legend | Well or Field | County | State or Country |
|---|---|---|---|---|---|---|---|
| 50 | 50 | Tertiary | | | River Junction | Uintah | Utah |
| 50 | 60 | Tertiary | Wasach | G | Bridger Lake | Summit | Utah |
| 140 | 60 | Tertiary | Kenai | | Nicolai A | C.I. | Alaska |
| >85 | 85 | Cretaceous | Mesa Verde | E | Patrick Draw | Swtwtr. | Wyo. |
| >85 | 85 | Cretaceous | Mesa Verde | E | Lookout Mtn. | Sublette | Wyo. |
| 140 | 100 | Cretaceous | Eutaw | A | Heidelberg | Jasper | Miss. |
| 140 | 110 | Cretaceous | Paluxy | A | Laurel | Jones | Miss. |
| 140 | 140 | Jurassic | Cotton Valley | A | Heidelberg | Jasper | Miss. |
| <100 | 150 | Jurassic | Dakota | F | Bridger Lake | Summit | Utah |
| <100 | 160 | Jurassic | Entrada | | Ashley Valley | Unitah | Utah |
| | 200 | Triassic | Moenkopi | | Grassy Trail | Emery | Utah |
| | 200 | Triassic | Upper Bunter | | Hewett N.Sea | | England |
| | 225 | Perm.-Tri. | | | Gassi-Touil | | Algeria |
| | 230 | Permian | Sadlerochit | | Prudhoe Bay | N.Slope | Alaska |
| 260 | 255 | Permian | Sprayberry | B | Jackson-Hughes | Andrews | Texas |
| 260 | 260 | Permian | Wolfcamp | B | Southland Roy. | Andrews | Texas |
| 260 | 265 | Permian | Dean | B | Hughes A | Andrews | Texas |
| 260 | 265 | Permian | Dean | C | Stout A | Reagan | Texas |
| 260 | 290 | Permian | San Andres | | Cummins | Ector | Texas |
| | 300 | Penn. | | | Wharton A | Sherman | Texas |
| | 320 | Penn. | Caddo Cong. | | Glass A | Montague | Texas |
| 325 | 335 | Miss. | | | Lisbon Unit | SanJuan | Utah |
| | 335 | Miss. | | | Blakemore | Beaver | Okla. |
| | 420 | Silurian | | | Fritchley | | Ohio |
| | 420 | Silurian | | D | D3—23 | | Libya |
| | 420 | Silurian | | D | Q1—23 | | Libya |
| 470> | 500 | U. Camb. | Ellenberger | | Continental S. | | Texas |
| | | | | | Alaskan Seep | C.I. | Alaska |
| | | | | | Uramu | | Papua |

| Source M.Y.[1] | Isoprenoids Measured By Carbon Number | | | | | | IGI[3] | Isoprenoid Profile | | | Pristane Index |
|---|---|---|---|---|---|---|---|---|---|---|---|
| | 20 | 19T | 18 | 16 | 15 | 14 | | Phytol | Biotic Prist. | Farnesol | |
| 50 | 45.9 | 33.7 | 14.5 | 4.3 | 1.7 | 0.0 | 2.45 | 0.85 | 0.15 | 0.00 | 0.40 |

Table I-continued

Isoprenoids Analyses

| | | | | | | | | | | | |
|---|---|---|---|---|---|---|---|---|---|---|---|
| 50 | 19.1 | 50.5 | 11.7 | 12.6 | 3.3 | 2.9 | 0.79 | 0.67 | 0.33 | 0.00 | 0.67 |
| 140 | 19.5 | 38.9 | 12.9 | 11.4 | 11.8 | 5.5 | 0.80 | 0.73 | 0.21 | 0.06 | 0.56 |
| >85 | 8.5 | 69.9 | 10.7 | 8.0 | 2.4 | 0.4 | 0.45 | 0.42 | 0.57 | 0.00 | 0.84 |
| >85 | 8.5 | 63.2 | 10.7 | 12.3 | 4.5 | 0.8 | 0.37 | 0.52 | 0.48 | 0.00 | 0.79 |
| 140 | 41.3 | 31.7 | 12.2 | 11.0 | 3.8 | 0.0 | 1.78 | 0.90 | 0.10 | 0.00 | 0.31 |
| 140 | 35.5 | 31.5 | 14.2 | 14.1 | 4.6 | 0.0 | 1.26 | 0.92 | 0.08 | 0.00 | 0.26 |
| 140 | 51.5 | 27.4 | 12.2 | 6.5 | 2.4 | 0.0 | 2.74 | 0.92 | 0.08 | 0.00 | 0.24 |
| <100 | 24.6 | 53.6 | 11.2 | 7.5 | 3.0 | 0.0 | 1.31 | 0.62 | 0.38 | 0.00 | 0.70 |
| <100 | 2.3 | 94.3 | 0.9 | 0.7 | 1.9 | 0.0 | 1.46 | 0.06 | 0.93 | 0.02 | 0.98 |
| | 23.8 | 26.7 | 12.0 | 13.7 | 15.1 | 8.7 | 0.93 | 0.81 | 0.07 | 0.11 | 0.28 |
| | (4) | | | | | | | | | | |
| | 23.4 | 52.3 | 12.0 | 12.3 | 0.0 | 0.0 | 0.96 | 0.66 | 0.34 | 0.00 | 0.66 |
| | 34.8 | 42.4 | 17.2 | 3.4 | 2.2 | 0.0 | 1.69 | 0.76 | 0.24 | 0.00 | 0.54 |
| 260 | 25.5 | 36.5 | 21.7 | 12.0 | 3.8 | 0.4 | 0.76 | 0.88 | 0.12 | 0.00 | 0.35 |
| 260 | 26.7 | 41.4 | 17.8 | 10.0 | 4.0 | 0.0 | 0.96 | 0.80 | 0.20 | 0.00 | 0.50 |
| 260 | 25.5 | 42.5 | 13.9 | 10.2 | 6.5 | 1.4 | 1.06 | 0.76 | 0.23 | 0.00 | 0.56 |
| 260 | 26.4 | 38.9 | 18.4 | 10.6 | 4.7 | 1.0 | 0.91 | 0.83 | 0.17 | 0.00 | 0.45 |
| 260 | 30.4 | 38.9 | 20.0 | 8.3 | 2.3 | 0.0 | 1.07 | 0.83 | 0.17 | 0.00 | 0.43 |
| | 36.0 | 35.1 | 19.4 | 7.7 | 1.8 | 0.0 | 1.33 | 0.88 | 0.12 | 0.00 | 0.35 |
| | 31.0 | 44.6 | 16.0 | 6.0 | 2.4 | 0.0 | 1.41 | 0.74 | 0.26 | 0.00 | 0.57 |
| 325 | 18.0 | 21.9 | 10.8 | 37.8 | 11.6 | 0.0 | 0.37 | 1.00 | 0.00 | 0.00 | 0.00 |
| | 34.8 | 44.2 | 14.6 | 4.4 | 1.9 | 0.0 | 1.82 | 0.74 | 0.26 | 0.00 | 0.58 |
| | 31.1 | 48.5 | 14.1 | 6.4 | 0.0 | 0.0 | 1.52 | 0.69 | 0.31 | 0.00 | 0.62 |
| | 31.2 | 46.9 | 13.3 | 6.2 | 2.0 | 0.4 | 1.60 | 0.70 | 0.30 | 0.00 | 0.62 |
| | 29.0 | 44.9 | 18.6 | 5.1 | 2.4 | 0.0 | 1.22 | 0.74 | 0.26 | 0.00 | 0.57 |
| 470> | (5) | | | | | | | | | | |
| | (5) | | | | | | | | | | |
| | 46.0 | 13.1 | 14.1 | 6.5 | 2.4 | 0.0 | 0.66 | 0.73 | 0.27 | 0.00 | 0.61 |

(1) Age of source rock, if known, millions of years
(2) Age of producing formation, millions of years
(3) Isoprenoid Generation Index
(4) No isoprenoids found
(5) ipC$_{18}$ and ipC$_{18}$ too low for accurate measurement Legend
- A — Crudes of common origin, Mississippi
- B — Crudes of common origin, Texas
- C — Crude of origin related to above
- D — Crudes of common origin, Libya
- E — Crudes of common origin, Wyoming
- F — Origin related to above
- F,G — Crudes from same field but not of common origin Isoprenoids were detected in all oils except an unusual n-alkane-free condensate from the North Sea Hewett field; hence, isoprenoids are shown to be common constituents of crude oils. In the cases of the Ellenberger crudes from Texas and an Alaska seep oil, the isoprenoid contents were low and only pristane and phytane could be measured reliably. n-Alkanes could not be detected in the upper Bunder and the Alsakan seep samples, which probably have been subjected to aerobic bidegradation. The common lack of detectable n-alkanes in seep oils and other oils that have been biogenetically altered has posed problems in correlating such oils because an OEP value cannot be obtained. However, it is expected that isoprenoids generally will be present in detectable quantities in such samples; hence, the isoprenoid-based origin-and genesis-diagnostic parameters should be especially useful.

Of the 26 remaining samples, only one lacked biotic pristane in the isoprenoid profile, whereas others had biotic pristane ranging up to 0.93. This demonstrates that pristane of biotic origin should be useful because it commonly occurs and varies significantly in quantity.

The data listed in Table I are in order of increasing geological age of the producing reservoir. Based on these data, there is no correlation between geological age and presence of measured components, calculated components or calculated parameters. This lack of correlation leads to two conclusions:

1. Although considerable variation may occur over the span of geological time during which most petroleum has been generated, there have been no fundamental changes in ecological, environmental or evolutionary factors to have altered that portion of the biosphere responsible for the presence of isoprenoids in oils. There is no evidence of predominance of biotic pristane or of farnesol at any particular geological time.

2. Assuming that geologically older crude oils have migrated from their respective source rock facies significantly earlier than crude oils of younger geological age, then the absence of a time-dependent trend for the Isoprenoid Generation Index (IGI) is interpreted as indicating that IGI is a function of the state of diagenesis at the time the crude oil migrated from the source rock and is not altered thereafter.

EXAMPLE II

A core sample was taken at a depth interval of 11,547 to 11,557 feet from a well in Collier County, Florida. The core sample was prepared for analysis by crushing, then grinding the sample to about 200 mesh. The resulting powder was exhaustively extracted in a Soxhlet apparatus with methylene chloride. The resulting extract was analyzed for isoprenoids substantially as described in Example I above. The results of this analysis are as follows:

| Components Measured | Weight Percent |
|---|---|
| Isoprenoids | |
| C20 (Phytane) | 59.23 |
| C19 (Pristane) | 31.94 |
| C18 | 6.94 |
| C16 | 1.52 |
| C15 (Farnesane) | 0.36 |
| C14 | 0.00 |

| Components Calculated | Weight Percent |
|---|---|
| Pristane from Phytol | 10.68 |
| Biotic Pristane | 21.26 |
| Farnesane from Phytol | 0.35 |
| Farnesane from Farnesol | 0.00 |

Calculated Parameters

| -continued | |
|---|---|
| Isoprenoid Generation Index, IGI | 7.00 |
| Pristane Index, P.I. | 0.50 |
| Pristane/Phytane Ratio | 0.54 |
| Isoprenoid Profile | |
| Phytol Isoprenoids | 0.79 |
| Biotic Pristane | 0.21 |
| Farnesol Isoprenoids | 0.00 |

Examination of the above data indicates that the sample rock is not a source rock. The IGI=7 indicates that diagenesis has not progressed enough to generate migratable petroleum hydrocarbons.

Reasonable variations and modifications, which will be apparent to those skilled in the art, can be made in this invention without departing from the spirit and scope thereof.

What is claimed is:

1. A method for geochemical exploration comprising the steps of:
   a. obtaining at least one rock sample from at least one location in the earth's crust; and
   b. analyzing said sample for isoprenoids to determine the ratio between the relative concentration of the $C_{20}$ isoprenoid and the sum of the $C_{18}$ and $C_{16}$ isoprenoids, wherein a ratio of less than 3:1 indicates a source rock.

2. A method for determining whether marine crude oils are of common origin which comprises:
   a. obtaining samples of at least two crude oils,
   b. analyzing said samples for isoprenoids to determine for each of said samples the ratio between the relative concentration of the $C_{19}$ isoprenoid of biotic origin and the total $C_{19}$ isoprenoids at a fixed degree of genesis, and
   c. correlating said ratios with each other.

3. A method for determining the source of an oil which comprises
   a. obtaining a sample of said oil,
   b. analyzing said oil for isoprenoids to determine the ratio between the relative concentration of the $C_{19}$ isoprenoid of biotic origin and the total $C_{19}$ isoprenoids at a degree of genesis of an IGI of 1.25, wherein IGI is the ratio between the relative concentration of the $C_{20}$ isoprenoid and the sum of the $C_{18}$ and $C_{16}$ isoprenoids,
   c. obtaining a sample of a source rock,
   d. analyzing said rock for isoprenoids to determine the ratio between the relative concentration of the $C_{19}$ isoprenoid of biotic origin and the total $C_{19}$ isoprenoids at a degree of genesis of an IGI of 1.25, and
   e. correlating said ratios determined in steps (b) and (d), wherein, approximate equivalence of said ratios is indicative that the rock is the geochemical source of the oil.

4. A method for determining whether crude oils are of common origin which comprises:
   a. obtaining samples of at least two crude oils,
   b. analyzing said samples for isoprenoids,
   c. determining for each of said samples the ratio between the relative concentration of the $C_{20}$ isoprenoid and the sum of the $C_{18}$ and $C_{16}$, and
   d. determining for each of said samples the relative weight fractions of isoprenoids from phytol, biotic and farnesol origins, wherein oils having approximately the same ratio and approximately the same relative weight fractions of isoprenoids from said three origins are of common origin.

* * * * *